(12) United States Patent
Cormier et al.

(10) Patent No.: US 7,455,654 B2
(45) Date of Patent: Nov. 25, 2008

(54) METHOD AND APPARATUS FOR REDUCING THE INCIDENCE OF TOBACCO USE

(75) Inventors: Michel J. N. Cormier, Mountain View, CA (US); Robert M. Gale, Los Gatos, CA (US); Andrew G. Scott, Palo Alto, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 10/971,224

(22) Filed: Oct. 21, 2004

(65) Prior Publication Data

US 2005/0089553 A1    Apr. 28, 2005

Related U.S. Application Data

(60) Provisional application No. 60/515,396, filed on Oct. 28, 2003.

(51) Int. Cl.
*A61M 37/00* (2006.01)
*A61M 5/00* (2006.01)

(52) U.S. Cl. .................. 604/46; 604/173; 424/448

(58) Field of Classification Search .............. 604/22, 604/117, 173, 239, 46, 500; 424/448
See application file for complete search history.

(56) References Cited

U.S. PATENT DOCUMENTS

| | | | |
|---|---|---|---|
| 3,136,314 A | 6/1964 | Kravitz | |
| RE25,637 E | 9/1964 | Kravitz et al. | |
| 3,814,097 A | 6/1974 | Ganderton et al. | |
| 3,964,482 A | 6/1976 | Gerstel et al. | |
| 4,109,655 A | 8/1978 | Chacornac | |
| 4,453,926 A | 6/1984 | Galy | |
| 5,120,546 A * | 6/1992 | Hansen et al. | 424/449 |
| 5,250,023 A | 10/1993 | Lee et al. | |
| 5,487,726 A | 1/1996 | Rabenau et al. | |
| 5,738,728 A | 4/1998 | Tisone | |
| 5,741,554 A | 4/1998 | Tisone | |
| 5,743,960 A | 4/1998 | Tisone | |
| 5,879,326 A | 3/1999 | Godshall et al. | |
| 5,916,524 A | 6/1999 | Tisone | |
| 6,050,988 A | 4/2000 | Zuck | |
| 6,083,196 A | 7/2000 | Trautman et al. | |
| 6,091,975 A | 7/2000 | Daddona et al. | |
| 6,230,051 B1 | 5/2001 | Cormier et al. | |
| 6,322,808 B1 | 11/2001 | Trautman et al. | |
| 6,855,131 B2 | 2/2005 | Trautman et al. | |
| 6,855,372 B2 | 2/2005 | Trautman et al. | |
| 6,918,901 B1 | 7/2005 | Theeuwes et al. | |

(Continued)

FOREIGN PATENT DOCUMENTS

WO    WO 93/17754    9/1993

(Continued)

*Primary Examiner*—Catherine S. Williams
(74) *Attorney, Agent, or Firm*—Marc Gorayeb; Kathleen Williams; Matthew Beaudet

(57) ABSTRACT

An apparatus for transdermally delivering a nicotine-based agent to a tobacco or nicotine user comprising a microprojection member having a plurality of microprojections that are adapted to pierce the stratum corneum of the tobacco user, the microprojection member having a biocompatible coating disposed thereon that includes a nicotine-based agent.

18 Claims, 2 Drawing Sheets

U.S. PATENT DOCUMENTS

| | | |
|---|---|---|
| 6,953,589 B1 | 10/2005 | Trautman et al. |
| 7,097,631 B2 | 8/2006 | Trautman et al. |
| 7,131,960 B2 | 11/2006 | Trautman et al. |
| 7,184,826 B2 | 2/2007 | Cormier et al. |
| 2002/0087182 A1 | 7/2002 | Trautman et al. |
| 2002/0091357 A1* | 7/2002 | Trautman et al. ........... 604/117 |
| 2002/0123675 A1 | 9/2002 | Trautman et al. |
| 2002/0128599 A1 | 9/2002 | Cormier et al. |
| 2002/0132054 A1 | 9/2002 | Trautman et al. |
| 2002/0177839 A1 | 11/2002 | Cormier |
| 2003/0181936 A1 | 9/2003 | Trautman et al. |
| 2003/0199810 A1 | 10/2003 | Trautman et al. |
| 2004/0062813 A1 | 4/2004 | Cormier et al. |
| 2004/0138610 A1 | 7/2004 | Cormier et al. |
| 2004/0236271 A1 | 11/2004 | Theeuwes et al. |
| 2004/0265354 A1 | 12/2004 | Ameri et al. |
| 2005/0106209 A1 | 5/2005 | Ameri et al. |
| 2005/0106227 A1 | 5/2005 | Zalipsky et al. |

FOREIGN PATENT DOCUMENTS

| | | |
|---|---|---|
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/11937 | 3/1998 |
| WO | WO 98/28037 | 7/1998 |
| WO | WO 98/29298 | 7/1998 |
| WO | WO 98/29365 | 7/1998 |
| WO | WO 99/64580 | 12/1999 |
| WO | WO 02/094368 | 11/2002 |

* cited by examiner

METHOD AND APPARATUS FOR REDUCING THE INCIDENCE OF TOBACCO USE

CROSS-REFERENCE TO RELATED APPLICATIONS

This application claims the benefit of U.S. Provisional Application No. 60/515,396, filed Oct. 28, 2003.

FIELD OF THE PRESENT INVENTION

The present invention relates to a method and apparatus for reducing or eliminating an individual's tobacco usage habit, particularly smoking, and the associated nicotine dependence that is created by the tobacco use.

BACKGROUND OF THE INVENTION

In recent years, with the recognition of the harmful effects of tobacco smoking, there have been numerous campaigns and programs by governmental agencies, various health groups and other interested organizations to disseminate information about the adverse health effects resulting from tobacco smoking. Moreover, and as a result of this recognition of the harmful effects, there have been many programs directed to attempts in reducing smoking incidence.

The successes in achieving reduction in the incidence of smoking have however been relatively poor with presently known techniques. The present state of the art involves both behavioral approaches and pharmacological approaches. Approximately 80% or more of the tobacco smokers who initially quit smoking after using some behavioral or pharmacological approach to singly reduce smoking incidence generally relapse and return to the habit of smoking at their former rate of smoking within about a one year's period of time.

One approach that is commonly employed to reduce the incidence of smoking relies upon nicotine containing chewing gum, which is designed to reduce smoking withdrawal symptoms. The reported success rate, while still relatively low, is approximately twice that of the other methods, which have heretofore been employed. There are numerous drawbacks and disadvantages associated with the use of the nicotine gum, including bad taste and destruction of dental appliances. A further disadvantage is that nicotine gum causes gastrointestinal upset, which often reduces compliance.

In addition, it has been found that the nicotine containing gum does not satisfy the craving that most smokers experience for the distinct sensations in the throat and chest elicited by nicotine in the smoke. Over the course of many years of tobacco smoking, these particular sensations have become an important part of and associated with the habit of smokers and give rise to tobacco smoke dependency in most of the tobacco smokers.

Passive transdermal delivery of nicotine-based agents has also been employed to reduce the incidence of smoking. The delivery is typically achieved via a transdermal patch that is releasably applied to the skin. Illustrative are the transdermal patches used in the system marketed by GlaxoSmithKline under the tradename NICODERM CQ®.

As is well known in the art, transdermal agent delivery systems generally rely on passive diffusion to administer an agent, such as nicotine, while active transdermal agent delivery systems rely on external energy sources, including electricity (e.g., iontophoresis) and ultrasound (e.g., phonophoresis) to deliver the agent. Passive transdermal drug delivery systems are more common.

Passive transdermal systems typically include a drug reservoir containing a high concentration of the agent. The reservoir is adapted to contact the skin, which enables the agent to diffuse through the skin and into the body tissues or bloodstream of an individual, such as a tobacco user.

As is well known in the art, transdermal agent flux is dependent upon the condition of the skin, the size and physical/chemical properties of the drug molecule, and the concentration gradient across the skin. Because of the low permeability of the skin to many agents, transdermal delivery has had limited applications. This low permeability is attributed primarily to the stratum corneum, the outermost skin layer which consists of flat, dead cells filled with keratin fibers (i.e., keratinocytes) surrounded by lipid bilayers. This highly-ordered structure of the lipid bilayers confers a relatively impermeable character to the stratum corneum.

One common method of enhancing the passive transdermal diffusional agent flux involves pre-treating the skin with, or co-delivering with the agent, a skin permeation enhancer. A permeation enhancer, when applied to a body surface through which the agent is delivered, enhances the flux of the agent therethrough. However, the efficacy of these methods in enhancing transdermal flux for many agents has been limited.

A further method of enhancing transdermal agent flux is through the use of active transport systems. As stated, active transport systems use an external energy source to assist and, in most instances, enhance agent flux through the stratum corneum. One such enhancement for transdermal agent delivery is referred to as "electrotransport." This mechanism uses an electrical potential, which results in the application of electric current to aid in the transport of the agent through a body surface, such as skin.

There also have been many techniques and systems developed to mechanically penetrate or disrupt the outermost skin layers thereby creating pathways into the skin in order to enhance the amount of agent being transdermally delivered. Early vaccination devices, known as scarifiers, generally included a plurality of tines or needles that were applied to the skin to and scratch or make small cuts in the area of application. The vaccine was applied either topically on the skin, such as disclosed in U.S. Pat. No. 5,487,726, or as a wetted liquid applied to the scarifier tines, such as disclosed in U.S. Pat. Nos. 4,453,926, 4,109,655, and 3,136,314.

There are, however, numerous disadvantages and drawbacks associated with scarifiers. A serious disadvantage in using a scarifier to deliver an agent is the difficulty in determining the transdermal agent flux and the resulting dosage delivered. Also, due to the elastic, deforming and resilient nature of skin to deflect and resist puncturing, the tiny piercing elements often do not uniformly penetrate the skin and/or are wiped free of a liquid coating of an agent upon skin penetration.

Additionally, due to the self healing process of the skin, the punctures or slits made in the skin tend to close up after removal of the piercing elements from the stratum corneum. Thus, the elastic nature of the skin acts to remove the active agent liquid coating that has been applied to the tiny piercing elements upon penetration of these elements into the skin. Furthermore, the tiny slits formed by the piercing elements heal quickly after removal of the device, thus limiting the passage of the liquid agent solution through the passageways created by the piercing elements and in turn limiting the transdermal flux of such devices.

Other systems and apparatus that employ tiny skin piercing elements to enhance transdermal drug delivery are disclosed in U.S. Pat. Nos. 5,879,326, 3,814,097, 5,250,023, 3,964,482, Reissue No. 25,637, and PCT Publication Nos. WO 96/37155, WO 96/37256, WO 96/17648, WO 97/03718, WO 98/11937, WO 98/00193, WO 97/48440, WO 97/48441, WO 97/48442, WO 99/64580, WO 98/28037, WO 98/29298, and WO 98/29365; all incorporated by reference in their entirety.

The disclosed systems and apparatus employ piercing elements of various shapes, sizes and arrays to pierce the outermost layer (i.e., the stratum corneum) of the skin. The piercing elements disclosed in these references generally extend perpendicularly from a thin, flat member, such as a pad or sheet. The piercing elements in some of these devices are extremely small, some having a microprojection length of only about 25-400 microns and a microprojection thickness of only about 5-50 microns. These tiny piercing/cutting elements make correspondingly small microslits/microcuts in the stratum corneum for enhancing transdermal agent delivery therethrough.

The disclosed systems further typically include a reservoir for holding the agent and also a delivery system to transfer the agent from the reservoir through the stratum corneum, such as by hollow tines of the device itself. One example of such a device is disclosed in WO 93/17754, which has a liquid agent reservoir. The reservoir must, however, be pressurized to force the liquid agent through the tiny tubular elements and into the skin. Disadvantages of such devices include the added complication and expense for adding a pressurizable liquid reservoir and complications due to the presence of a pressure-driven delivery system.

As disclosed in U.S. patent application Ser. No. 10/045, 842, which is fully incorporated by reference herein, it is also possible to have the agent that is to be delivered coated on the microprojections instead of contained in a physical reservoir. This eliminates the necessity of a separate physical reservoir and developing a drug formulation or composition specifically for the reservoir.

Heretofore, however, coated microprojections have not been employed to transdermally deliver nicotine-based agents to tobacco or nicotine users to reduce the dependency thereon.

It is therefore an object of the present invention to provide a transdermal delivery apparatus and method that substantially reduces or eliminates the aforementioned drawbacks and disadvantages associated with prior art nicotine-based agent delivery systems.

It is another object of the present invention to provide a transdermal apparatus and method for the delivery of nicotine-based agents that substantially reduces or eliminates the incidence of tobacco and/or nicotine use.

It is another object of the present invention to provide a transdermal delivery apparatus having a coated microprojection array that delivers nicotine-based agents at an effective dose in a bolus delivery.

SUMMARY OF THE INVENTION

In accordance with the above objects and those that will be mentioned and will become apparent below, the apparatus for transdermally delivering nicotine-based agents to a tobacco or nicotine user in accordance with this invention comprises a microprojection member having a plurality of microprojections that are adapted to pierce through the stratum corneum into the underlying epidermis and dermis layers of the nicotine user, the microprojection member having a biocompatible coating having at least one nicotine-based agent disposed thereon. Preferably, the nicotine-based agent is selected from the group consisting of nicotine base, nicotine salts and simple derivatives of nicotine.

As discussed in detail herein, upon piercing through the stratum corneum, the agent-containing coating is dissolved by body fluid (intracellular fluids and extracellular fluids, such as interstitial fluid) and released into the epidermis layer for systemic therapy (i.e., bolus delivery). The advantages of the invention thus include (i) effective transdermal bolus delivery of nicotine-based agents, (ii) rapid administration or on-set of nicotine, and (iii) effective treatment for breakthrough craving during tobacco quit attempts by administering small amounts of nicotine when needed. The invention further provides a convenient and easy to use method for supplementing nicotine replacement therapy.

Preferably, each of the microprojections has a length of less than 1000 microns, more preferably, less than 500 microns. In one embodiment of the invention, each microprojection has a length less than 250 microns.

The coating formulations that are employed to form the biocompatible coatings preferably include at least one wetting agent and, optionally, a hydrophilic polymer.

Preferably, the coating formulations include at least one surfactant, including, but not limited to, sodium lauroamphoacetate, sodium dodecyl sulfate (SDS), cetylpyridinium chloride (CPC), dodecyltrimethyl ammonium chloride (TMAC), benzalkonium, chloride, polysorbates such as Tween 20 and Tween 80, other sorbitan derivatives such as sorbitan laurate, and alkoxylated alcohols such as laureth-4. Most preferred surfactants include Tween 20, Tween 80, and SDS.

The coating formulations further preferably include at least one polymeric material that has amphiphilic properties, including, but not limited to, cellulose derivatives, such as hydroxyethylcellulose (HEC), hydroxypropylmethylcellulose (HPMC), hydroxypropycellulose (HPC), methylcellulose (MC), hydroxyethylmethylcellulose (HEMC), and ethylhydroxyethylcellulose (EHEC), as well as pluronics.

The coating formulations can further include a hydrophilic polymer. Preferably the hydrophilic polymer is selected from the following group: poly(vinyl alcohol), poly(ethylene oxide), poly(2-hydroxyethylmethacrylate), poly(n-vinyl pyrolidone), polyethylene glycol and mixtures thereof, and like polymers.

In a further embodiment of the invention, the coating formulations and, hence, biocompatible coatings include a vasoconstrictor. Preferably, the vasoconstrictor is selected from the group consisting of amidephrine, cafaminol, cyclopentamine, deoxyepinephrine, epinephrine, felypressin, indanazoline, metizoline, midodrine, naphazoline, nordefrin, octodrine, omipressin, oxymethazoline, phenylephrine, phenylethanolamine, phenylpropanolamine, propylhexedrine, pseudoephedrine, tetrahydrozoline, tramazoline, tuaminoheptane, tymazoline, vasopressin and xylometazoline.

In a further embodiment of the invention, the coating formulations and, hence, biocompatible coatings, can further include a biocompatible carrier. Examples of biocompatible carriers include human albumin, bioengineered human albumin, polyglutamic acid, polyaspartic acid, polyhistidine, pentosan polysulfate, polyamino acids, sucrose, trehalose, melezitose, raffinose and stachyose.

The thickness of the biocompatible coating disposed on the microprojections is preferably less than 50 microns. In one embodiment of the invention, the coating thickness is less than 25 microns.

The biocompatible coating provides a biologically effective amount of the nicotine-based agent and, if employed, a biologically effective amount of the vasoconstrictor.

The biocompatible coating can be applied to and dried on the microprojections using known coating methods. For example, the microprojections can be immersed or partially immersed into an aqueous coating solution. Alternatively, the coating solution can be sprayed onto the microprojections. Preferably, the spray has a droplet size of about 10-200 picoliters. More preferably, the droplet size and placement is precisely controlled using printing techniques so that the coating solution is deposited directly onto the microprojections and not onto other "non-piercing" portions of the member having the microprojections.

The method for transdermally delivering a nicotine-based agent to a nicotine user, in accordance with one embodiment of the invention, comprises the steps of (i) providing a microprojection member having a plurality of microprojections that are adapted to pierce the stratum corneum of the nicotine user, (ii) coating the microprojection member with a coating formulation having at least one nicotine-based agent to form a biocompatible coating and (iii) applying the microprojection member to the skin of the nicotine user, whereby the microprojection members pierce the stratum corneum of the nicotine user and deliver the biocompatible coating and, hence, nicotine-based agent disposed therein.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
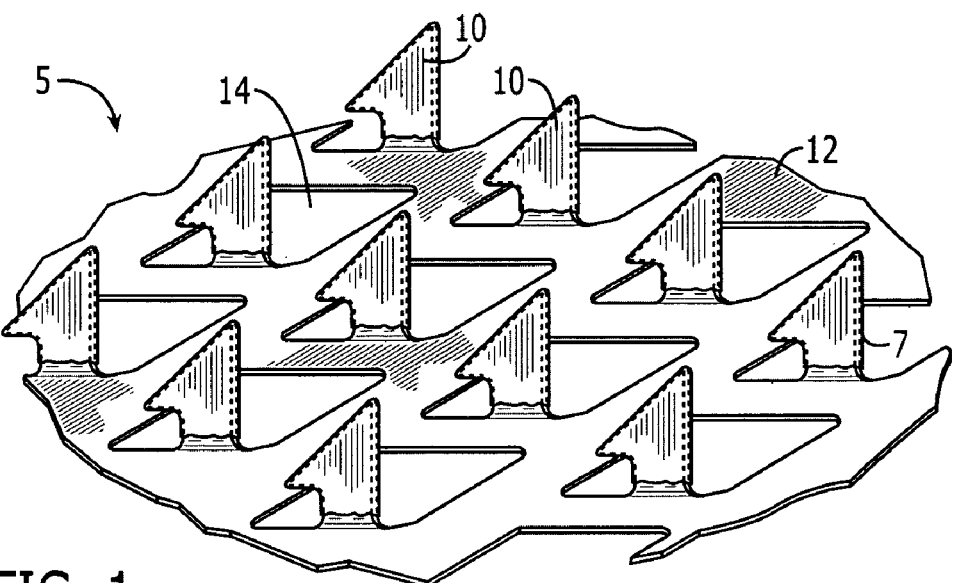
FIG. 1 is a perspective view of a portion of one example of a microprojection array.

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a", "an" and "the" include plural referents unless the content clearly dictates otherwise. Thus, for example, reference to "a nicotine-based agent" includes two or more such agents; reference to "a microprojection" includes two or more such microprojections and the like.

Definitions

The terms "biologically active agent", "active agent" and "agent", as used herein, refer to a composition of matter or mixture containing a substance or drug, such as the nicotine-based agents described below, that are pharmacologically effective when administered in a therapeutically effective amount.

The term "nicotine-based agent", as used herein, means and includes nicotine, a substance equivalent to or approximating nicotine, including any and all known compounds and/or compositions that produce a similar physiological effect as nicotine, or a mixture thereof that produces a similar effect as nicotine. The term "nicotine-based agent" thus includes, but is not limited to, nicotine base, nicotine salts and simple derivatives of nicotine.

Examples of pharmaceutically acceptable nicotine salts include, but are not limited to, acetate, propionate, butyrate, pentanoate, hexanoate, heptanoate, levulinate, chloride, bromide, citrate, succinate, maleate, glycolate gluconate, glucuronate, 3-hydroxyisobutyrate, 2-hydroxyisobutyrate, lactate, malate, pyruvate, fumarate, tartarate, tartronate, nitrate, phosphate, benzene sulfonate, methane sulfonate, sulfate, sulfonate, salycilate and double salts such as zinc chloride.

Examples of simple nicotine derivatives include, but are not limited to, amides, carbamates, imines, enamines, and N-acyloxyalkyloxycarbonyls.

The noted nicotine-based agents can also be in various forms, such as free bases, acids, charged or uncharged molecules, components of molecular complexes or nonirritating, pharmacologically acceptable salts.

The term "transdermal", as used herein, means the delivery of an agent into and/or through the skin for systemic therapy.

The term "transdermal flux", as used herein, means the rate of transdermal delivery.

The term "co-delivering", as used herein, means that a supplemental agent(s) is administered transdermally either before the agent is delivered, before and during transdermal flux of the agent, during transdermal flux of the agent, during and after transdermal flux of the agent, and/or after transdermal flux of the agent. Additionally, two or more nicotine-based agents may be coated onto the microprojections resulting in co-delivery of the nicotine-based agents.

It is to be understood that more than one nicotine-based agent can be incorporated into the coating formulations and, hence, biocompatible coatings of this invention and that the use of the terms "active agent" and/or "nicotine-based agent" in no way excludes the use of two or more such agents.

The term "biologically effective amount" or "biologically effective rate" shall be used when the nicotine-based agent is a pharmaceutically active agent and refers to the amount or rate of the pharmacologically active agent needed to effect the desired therapeutic, often beneficial, result. The amount of active agent employed in the coatings of the invention will be that amount necessary to deliver a therapeutically effective amount of the active agent to achieve the desired therapeutic result. In practice, this will vary widely depending upon the particular pharmacologically active agent being delivered, the site of delivery, the severity of the condition being treated, the desired therapeutic effect and the dissolution and release kinetics for delivery of the agent from the coating into skin tissues.

The term "bolus delivery" refers to "release of the nicotine-based agent into the skin within a certain time".

The term "release of the nicotine-based agent into the skin within a certain time" means that most (e.g., greater than 50%) of the total delivered dose into the skin is actually delivered during that time. The term does not refer to the total wearing time (which may be longer) or to the total amount of the agent coated on the microprojections.

The term "biologically effective amount" or "biologically effective rate" shall also be used when the nicotine-based agent is an immunologically active agent and refers to the amount or rate of the immunologically active agent needed to stimulate or initiate the desired immunologic, often beneficial result. The amount of the immunologically active agent employed in the coatings of the invention will be that amount necessary to deliver an amount of the active agent needed to achieve the desired immunological result. In practice, this will vary widely depending upon the particular immunologically active agent being delivered, the site of delivery, and the dissolution and release kinetics for delivery of the active agent into skin tissues.

The terms "microprojections" and "microprotrusions", as used herein, refer to piercing elements that are adapted to pierce or cut through the stratum corneum into the underlying epidermis layer, or epidermis and dermis layers, of the skin of a living animal, particularly a mammal and more particularly a human.

As discussed herein, in one embodiment of the invention, the microprojections have a projection length less than 1000 microns. In a further embodiment, the microprojections have a projection length of less than 500 microns, more preferably, less than 250 microns. The microprojections preferably have a width and thickness of about 5 to 50 microns. The microprojections can also be formed in different shapes, such as needles, blades, pins, punches, and combinations thereof.

The term "microprojection array", as used herein, refers to a plurality of microprojections arranged in an array for piercing the stratum corneum. The microprojection array can be formed by etching or punching a plurality of microprojections from a thin sheet and folding or bending the microprojections out of the plane of the sheet to form a configuration, such as that shown in FIG. 1. The microprojection array can also be formed in other known manners, such as by forming one or more strips having microprojections along an edge of each of the strip(s) as disclosed in U.S. Pat. No. 6,050,988, which is incorporated by reference herein in its entirety.

References to the area of the sheet or member and reference to some property per area of the sheet or member are referring to the area bounded by the outer circumference or border of the sheet.

The term "solution" shall include not only compositions of fully dissolved components but also suspensions of nicotine-based agents.

The present invention, as described herein, provides an effective method and apparatus to reduce or eliminate an individual's tobacco or nicotine usage habit, particularly smoking, as well as the nicotine dependency associated with that habit. The reduction or elimination of tobacco usage is accomplished with or without behavioral intervention. Such a strategy expands the use of nicotine replacement therapy from an abrupt tobacco usage cessation to a gradual reduction. Gradually reducing the number of cigarettes smoked or other nicotine products used while replacing the nicotine with an alternative source, such as the coated microprojection member of the invention, aids in reducing nicotine cravings and withdrawal thereby facilitating reduction or elimination of tobacco usage.

As indicated above, the present invention comprises an apparatus and system for transdermal delivery of nicotine-based agents to a tobacco or nicotine user. The system generally includes a microprojection member having a microprojection array comprising a plurality of microprojections that are adapted to pierce through the stratum corneum into the underlying epidermis layer, or epidermis and dermis layers.

Preferably, the microprojections have a coating thereon that contains at least one biologically active agent, more preferably, a nicotine-based agent. Upon piercing through the stratum corneum layer of the skin, the agent-containing coating is dissolved by body fluid (intracellular fluids and extracellular fluids such as interstitial fluid) and released into the epidermis layer for systemic therapy (i.e., bolus delivery).

In contrast, in a conventional passive patch, the agent-containing coating must diffuse into and through the stratum corneum to achieve systemic delivery. Thus, such systems do not exhibit bolus delivery.

Preferably, release of the nicotine-based agent into the epidermis layer of the skin occurs within 1 hour following application of the microprojection array. More preferably, release of the nicotine-based agent into the epidermis layer occurs within 15 min following application of the microprojection array. Even more preferably, release of the nicotine-based agent into the epidermis layer occurs within 5 min following application of the microprojection array.

According to the invention, the kinetics of the coating dissolution and release will depend on many factors including the nature of the biologically active agent, the coating process, the coating thickness and the coating composition (e.g., the presence of coating formulation additives). Depending on the release kinetics profile, it may be necessary to maintain the coated microprojections in piercing relation with the skin for extended periods of time. This can be accomplished by anchoring the microprojection member to the skin using adhesives or by using anchored microprojections, such as described in PCT Publication WO 97/48440, which is incorporated by reference herein in its entirety.

Referring now to FIG. 1, there is shown one embodiment of a microprojection member 5 for use with the present invention. As illustrated in FIG. 1, the microprojection member 5 includes a microprojection array 7 having a plurality of microprojections 10. The microprojections 10 preferably extend at substantially a 90° angle from the sheet 12, which includes openings 14.

Figure 3:
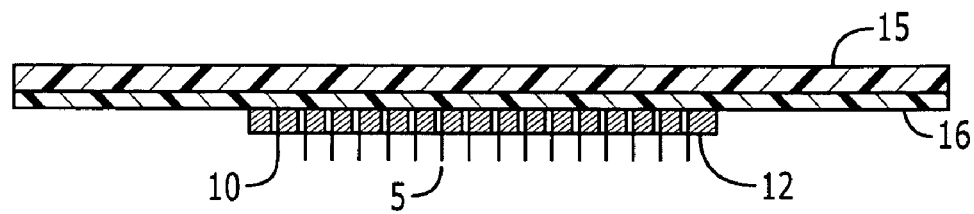
FIG. 3 is a side sectional view of a microprojection array having an adhesive backing.

According to the invention, the sheet 12 may be incorporated into a delivery patch, including a backing 15 for the sheet 12, and may additionally include adhesive 16 for adhering the patch to the skin (see FIG. 3). In this embodiment, the microprojections 10 are formed by etching or punching a plurality of microprojections 10 from a thin metal sheet 12 and bending the microprojections 10 out of the plane of the sheet 12.

The microprojection member 5 can be manufactured from various metals, such as stainless steel, titanium, nickel titanium alloys, or similar biocompatible materials, such as polymeric materials. Preferably, the microprojection member 5 is manufactured out of titanium.

Microprojection members that can be employed with the present invention include, but are not limited to, the members disclosed in U.S. Pat. Nos. 6,083,196, 6,050,988 and 6,091,975, which are incorporated by reference herein in their entirety.

Other microprojection members that can be employed with the present invention include members formed by etching silicon using silicon chip etching techniques or by molding plastic using etched micro-molds, such as the members disclosed U.S. Pat. No. 5,879,326, which is incorporated by reference herein in its entirety.

Figure 2:
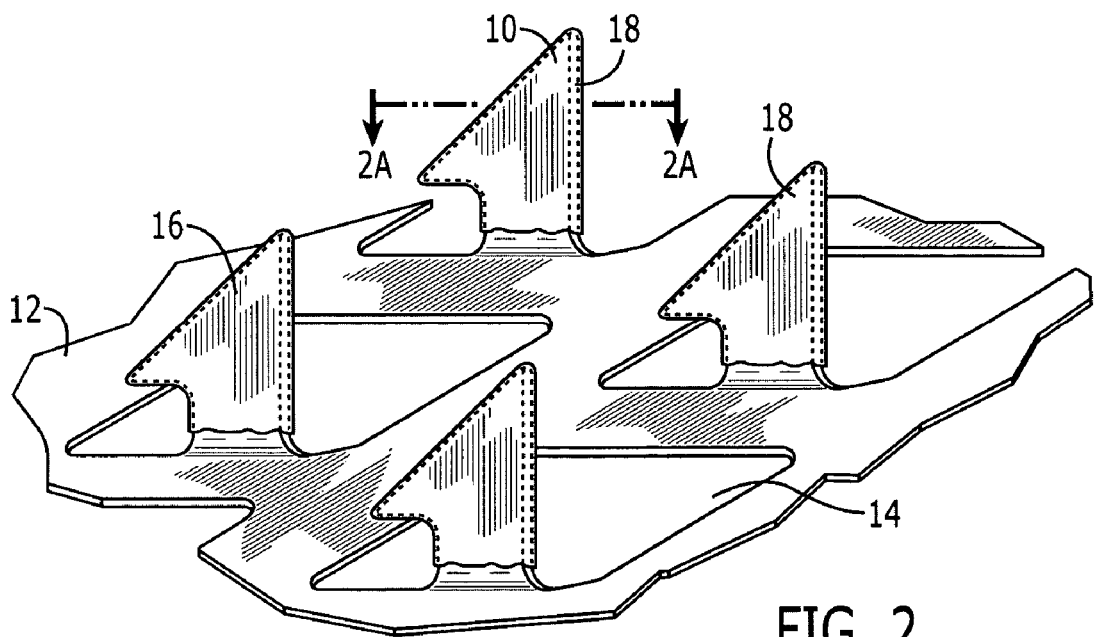
FIG. 2 is a perspective view of the microprojection array shown in FIG. 1 having a coating deposited on the microprojections, according to the invention.

Referring now to FIG. 2, there is shown the microprojection member 5 having microprojections 10 that include a biocompatible coating 16. According to the invention, the coating 16 can partially or completely cover each microprojection 10. For example, the coating 16 can be in a dry pattern coating on the microprojections 10. The coating 16 can also be applied before or after the microprojections 10 are formed.

According to the invention, the coating 16 can be applied to the microprojections 10 by a variety of known methods. Preferably, the coating is only applied to those portions the microprojection member 5 or microprojections 10 that pierce the skin (e.g., tips 18).

One such coating method comprises dip-coating. Dip-coating can be described as a means to coat the microprojections by partially or totally immersing the microprojections 10 into a coating solution. By use of a partial immersion technique, it is possible to limit the coating 16 to only the tips 18 of the microprojections 10.

A further coating method comprises roller coating, which employs a roller coating mechanism that similarly limits the coating 16 to the tips 18 of the microprojections 10. The roller coating method is disclosed in U.S. application Ser. No. 10/099,604 (Pub. No. 2002/0132054), which is incorporated by reference herein in its entirety.

Figure 2A:
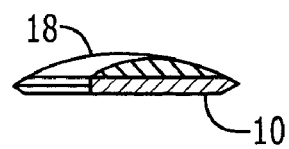
FIG. 2A is a cross-sectional view of a single microprojection taken along line 2A-2A in FIG. 2, according to the invention.

As discussed in detail in the noted application, the disclosed roller coating method provides a smooth coating that is not easily dislodged from the microprojections 10 during skin piercing. The smooth cross-section of the microprojection tip coating is further illustrated in FIG. 2A.

According to the invention, the microprojections 10 can further include means adapted to receive and/or enhance the volume of the coating 16, such as apertures (not shown), grooves (not shown), surface irregularities (not shown) or similar modifications, wherein the means provides increased surface area upon which a greater amount of coating can be deposited.

Another coating method that can be employed within the scope of the present invention comprises spray coating. According to the invention, spray coating can encompass formation of an aerosol suspension of the coating composition. In one embodiment, an aerosol suspension having a droplet size of about 10 to 200 picoliters is sprayed onto the microprojections 10 and then dried.

Pattern coating can also be employed to coat the microprojections 10. The pattern coating can be applied using a dispensing system for positioning the deposited liquid onto the microprojection surface. The quantity of the deposited liquid is preferably in the range of 0.1 to 20 nanoliters/microprojection. Examples of suitable precision-metered liquid dispensers are disclosed in U.S. Pat. Nos. 5,916,524; 5,743,960; 5,741,554; and 5,738,728; which are fully incorporated by reference herein.

Microprojection coating solutions can also be applied using ink jet technology using known solenoid valve dispensers, optional fluid motive means and positioning means which is generally controlled by use of an electric field. Other liquid dispensing technology from the printing industry or similar liquid dispensing technology known in the art can be used for applying the pattern coating of this invention.

According to the invention, the coating formulations applied to the microprojection member to form solid coatings can comprise aqueous and non-aqueous formulations having at least one nicotine-based agent. According to the invention, the active agent can be dissolved within a biocompatible carrier or suspended within the carrier.

Preferably, the nicotine-based agent comprises nicotine base, nicotine salts, and simple derivatives of nicotine. More preferably, the nicotine-based agent is a salt of nicotine.

There are several advantages related to the use of a salt instead of the base. First, use of a nicotine salt is expected to result in the reduction or elimination of skin depot as compared to nicotine base. Another advantage is that the salt form of nicotine is expected to result in improved nicotine chemical stability and improved stability of the chemical composition of the coating during storage as compared to nicotine base. A further advantage is that the salt form of nicotine is expected to reduce or eliminate the bad smell characteristic of nicotine base.

Examples of pharmaceutically acceptable nicotine salts include, but are not limited to, acetate, propionate, butyrate, pentanoate, hexanoate, heptanoate, levulinate, chloride, bromide, citrate, succinate, maleate, glycolate gluconate, glucuronate, 3-hydroxyisobutyrate, 2-hydroxyisobutyrate, lactate, malate, pyruvate, fumarate, tartarate, tartronate, nitrate, phosphate, benzene sulfonate, methane sulfonate, sulfate, sulfonate, salycilate and double salts such as zinc chloride.

Examples of simple nicotine derivatives include, but are not limited to, amides, carbamates, imines, enamines, and N-acyloxyalkyloxycarbonyls. Preferably these derivatives are reversible and will degrade or be metabolized to nicotine once introduced into the body.

Even more preferably, the nicotine-based agent is a salt of nicotine presenting low volatility. Use of this type of salts is expected to result in optimal stability of the chemical composition of the coating during storage. The solid coating is obtained by drying a formulation on the microprojection as described in U.S. patent application 2002/0128599. A number of factors affect the volatility of compounds. These include temperature, atmospheric pressure, and vapor pressure of the compound. The volatilization process is time dependant.

In addition, ionized compounds present a much lower volatility as compared to their unionized forms. For example, acetic acid presents a boiling point of 118° C. while sodium acetate is essentially non-volatile. During the drying process, all volatiles, including water are mostly removed. If a volatile compound in equilibrium between its ionized and non-ionized forms is present in solution, only the non-ionized form disappears from the formulation at the time where the drying process takes place and the ionized form stays in solution.

In a solid coating on a microprojection array, the active agent is typically present in an amount of less than about 2 mg per unit dose. With the addition of excipients and counterions, the total mass of solid coating is less than 4 mg per unit dose.

The microprojection array is usually disposed on an adhesive backing, which is attached to a disposable polymeric retainer ring. This assembly is typically packaged individually in a pouch or a polymeric housing. In addition to the assembly, this package contains an atmosphere (usually inert) that represents a volume of at least 3 mL. This large volume (as compared to that of the coating) acts as a sink for any volatile component. For example, at 20° C., the amount of acetic acid present in a 3 mL atmosphere as a result of its vapor pressure would be about 0.15 mg. This amount is typically what would be present in the solid coating if acetic acid were used as a counterion. In addition, components of the assembly such as the adhesive are likely to act as additional sinks for volatile components. As a result, during long-term storage, it is likely that the concentration of any volatile component present in the coating would change dramatically. These conditions are atypical of packaging of pharmaceutical compounds where large amounts of additives are usually present. Nicotine base also presents some volatility and, if present in the formulation, will likely be affected similarly by these processes.

Selection of a salt of nicotine presenting low volatility is based on the pKa of nicotine as well as the pKa and melting point of the acidic counterion. As is well known in the art, nicotine itself is a liquid at room temperature and presents some volatility. The smell of nicotine base is indeed very strong and this smell (which is partly due to volatile degradants) is greatly reduced by salification. Indeed most, if not all, nicotine salts present a higher melting point than nicotine itself. In addition, if nicotine salification is accomplished with an acidic compound having a pKa greater than about 4, a fraction of the acid and/or nicotine will be free and the counterion will slowly evaporate and/or migrate in system components, which will result in poor stability of the system. Examples of volatile counterions include, but are not limited to, acetic acid, propionic acid and butyric acid.

A most preferred embodiment is directed to nicotine salts with low volatility, wherein the counterion is a strong acid. A strong acid is defined as an acidic compound presenting at least one pKa lower than about 2. Examples of such acids include hydrochloric acid, hydrobromic acid, nitric acid, sulfonic acid, sulfuric acid, maleic acid, phosphoric acid, benzene sulfonic acid and methane sulfonic acid.

In another most preferred embodiment, the acidic counterion is a weak acid with low volatility. Such a compound is defined as an acidic compound presenting at least one pKa higher than about 2 and a melting point higher than about 50° C. Examples of such acids include citric acid, succinic acid, glycolic acid, gluconic acid, glucuronic acid, lactic acid, malic acid, pyruvic acid, tartaric acid, tartronic acid, fumaric acid, and salycilic acid.

According to the invention, nicotine and the counterion can be combined in various stoichiometric amounts. Excess of counterion (as the free acid or as a salt) can be added to nicotine in order to control pH. Mixtures of different counterions can also be used.

The coating formulation containing a nicotine-based agent would be preferably aqueous-based. Following drying, as described in U.S. Patent Application 2002/0128599 (World publication WO02/094368), the formulation is substantially free of water, although residual water may be present at up to 10 wt %.

Optionally the nicotine-based agent could be formulated in non-aqueous formulations. Examples of solvents that could be used include ethanol, IPA, chloroform, ether, petroleum ether, kerosene, and other volatile solvents. Formulations additives (wetting agents, viscosity enhancing agents) can also be added to the formation. Following drying, the formulation is substantially free of volatile solvent although residual solvent may be present at up to 10 wt %.

The concentration of the nicotine-based agent in the coating formulation is preferably in the range of approximately 5-80 wt. %, more preferably, in the range of approximately 10-70 wt. %. Even more preferably, the concentration of the nicotine-based agent in the coating formulation is in the range of approximately 20-60 wt. % of the coating formulation.

The concentration of the nicotine-based agent in the solid coating(s) is preferably up to approximately 99 wt. %. More preferably, the concentration of the nicotine-based agent in the solid coating(s) is in the range of approximately 30-70 wt. %.

According to the invention, the nicotine-based agent used in the present invention requires that the total amount of the agent coated on the microprojections of a microprojection array be sufficient to effectively delivery in the range of approximately 0.02-2.0 mg of the agent to a nicotine user. According to the invention, amounts within this range can be coated onto a microprojection array of the type shown in FIG. 1 having an area of up to 10 $cm^2$ and a microprojection density of up to 2000 microprojections per $cm^2$.

According to the invention, the coating formulations preferably include at least one wetting agent. As is well known in the art, wetting agents can generally be described as amphiphilic molecules. When a solution containing the wetting agent is applied to a hydrophobic substrate, the hydrophobic groups of the molecule bind to the hydrophobic substrate, while the hydrophilic portion of the molecule stays in contact with water. As a result, the hydrophobic surface of the substrate is not coated with hydrophobic groups of the wetting agent, making it susceptible to wetting by the solvent. Wetting agents include surfactants as well as polymers presenting amphiphillic properties.

In one embodiment of the invention, the coating formulations include at least one surfactant. According to the invention, the surfactant(s) can be zwitterionic, amphoteric, cationic, anionic, or nonionic. Examples of surfactants include, sodium lauroamphoacetate, sodium dodecyl sulfate (SDS), cetylpyridinium chloride (CPC), dodecyltrimethyl ammonium chloride (TMAC), benzalkonium, chloride, polysorbates such as Tween 20 and Tween 80, other sorbitan derivatives such as sorbitan laurate, and alkoxylated alcohols such as laureth-4. Most preferred surfactants include Tween 20, Tween 80, and SDS.

Applicants have found that the use of the noted surfactants in the desired ranges provides maximum wetting at and above the critical micelle concentration (CMC). Wetting is also noticeable at concentrations as low as about one order of magnitude below the CMC.

Preferably, the concentration of the surfactant is in the range of approximately 0.001-2 wt. % of the coating solution formulation.

In a further embodiment of the invention, the coating formulations include at least one polymeric material or polymer that has amphiphilic properties. Examples of the noted polymers include, without limitation, cellulose derivatives, such as hydroxyethylcellulose (HEC), hydroxypropylmethylcellulose (HPMC), hydroxypropycellulose (HPC), methylcellulose (MC), hydroxyethylmethylcellulose (HEMC), or ethylhydroxyethylcellulose (EHEC), as well as pluronics.

In one embodiment of the invention, the concentration of the polymer presenting amphiphilic properties is preferably in the range of approximately 0.01-20 wt. %, more preferably, in the range of approximately 0.03-10 wt. % of the coating formulation. Even more preferably, the concentration of the wetting agent is in the range of approximately 0.1-5 wt. % of the coating formulation.

As will be appreciated by one having ordinary skill in the art, the noted wetting agents can be used separately or in combinations.

According to the invention, the coating formulations can further include a hydrophilic polymer. Preferably the hydrophilic polymer is selected from the following group: poly (vinyl alcohol), poly(ethylene oxide), poly(2-hydroxyethylmethacrylate), poly(n-vinyl pyrolidone), polyethylene glycol and mixtures thereof, and like polymers. As is well known in the art, the noted polymers increase viscosity.

The concentration of the hydrophilic polymer in the coating formulation is preferably in the range of approximately 0.01-20 wt. %, more preferably, in the range of approximately 0.03-10 wt. % of the coating formulation. Even more preferably, the concentration of the wetting agent is in the range of approximately 0.1-5 wt. % of the coating formulation.

According to the invention, the coating formulations can further include a biocompatible carrier such as those disclosed in Co-Pending U.S. application Ser. No. 10/127,108, which is incorporated by reference herein in its entirety. Examples of biocompatible carriers include human albumin, bioengineered human albumin, polyglutamic acid, polyaspartic acid, polyhistidine, pentosan polysulfate, polyamino acids, sucrose, trehalose, melezitose, raffinose and stachyose.

The concentration of the biocompatible carrier in the coating formulation is preferably in the range of approximately 2-70 wt. %, more preferably, in the range of approximately 5-50 wt. % of the coating formulation. Even more preferably, the concentration of the wetting agent is in the range of approximately 10-40 wt. % of the coating formulation.

The coatings of the invention can further include a vasoconstrictor such as those disclosed in Co-Pending U.S. application Ser. Nos. 10/674,626 and 60/514,433, which are incorporated by reference herein in their entirety. As set forth in the noted Co-Pending Applications, the vasoconstrictor is used to control bleeding during and after application on the microprojection member. Preferred vasoconstrictors include, but are not limited to, amidephrine, cafaminol, cyclopentamine, deoxyepinephrine, epinephrine, felypressin, indanazoline, metizoline, midodrine, naphazoline, nordefrin, octodrine, ornipressin, oxymethazoline, phenylephrine, phenylethanolamine, phenylpropanolamine, propylhexedrine, pseudoephedrine, tetrahydrozoline, tramazoline, tuaminoheptane, tymazoline, vasopressin, xylometazoline and the mixtures thereof. The most preferred vasoconstrictors include epinephrine, naphazoline, tetrahydrozoline indanazoline, metizoline, tramazoline, tymazoline, oxymetazoline and xylometazoline.

The concentration of the vasoconstrictor, if employed, is preferably in the range of approximately 0.1 wt. % to 10 wt. % of the coating.

In yet another embodiment of the invention, the coating formulations include at least one "pathway patency modulator", such as those disclosed in Co-Pending U.S. application Ser. No. 09/950,436, which is incorporated by reference herein in its entirety. As set forth in the noted Co-Pending Application, the pathway patency modulators prevent or diminish the skin's natural healing processes thereby preventing the closure of the pathways or microslits formed in the stratum corneum by the microprojection member array. Examples of pathway patency modulators include, without limitation, osmotic agents (e.g., sodium chloride), and zwitterionic compounds (e.g., amino acids).

The term "pathway patency modulator", as defined in the Co-Pending Application, further includes anti-inflammatory agents, such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, aspirin and EDTA.

According to the invention, the coating formulations can also include a non-aqueous solvent, such as ethanol, chloroform, ether, propylene glycol, polyethylene glycol and the like, dyes, pigments, inert fillers, permeation enhancers, excipients, and other conventional components of pharmaceutical products or transdermal devices known in the art.

Other known formulation adjuvants can also be added to the coating formulations as long as they do not adversely affect the necessary solubility and viscosity characteristics of the coating formulation and the physical integrity of the dried coating.

Preferably, the coating formulations have a viscosity less than approximately 500 centipoise and greater than 3 centipoise in order to effectively coat each microprojection 10. More preferably, the coating formulations have a viscosity in the range of approximately 3-200 centipoise.

According to the invention, the desired coating thickness is dependent upon the density of the microprojections per unit area of the sheet and the viscosity and concentration of the coating composition as well as the coating method chosen. Preferably, the coating thickness is less than 50 microns.

In one embodiment, the coating thickness is less than 25 microns, more preferably, less than 10 microns as measured from the microprojection surface. Even more preferably, the coating thickness is in the range of approximately 1 to 10 microns.

In all cases, after a coating has been applied, the coating formulation is dried onto the microprojections 10 by various means. In a preferred embodiment of the invention, the coated member 5 is dried in ambient room conditions. However, various temperatures and humidity levels can be used to dry the coating formulation onto the microprojections. Additionally, the coated member 5 can be heated, lyophilized, freeze dried or similar techniques used to remove the water from the coating.

Figure 4:
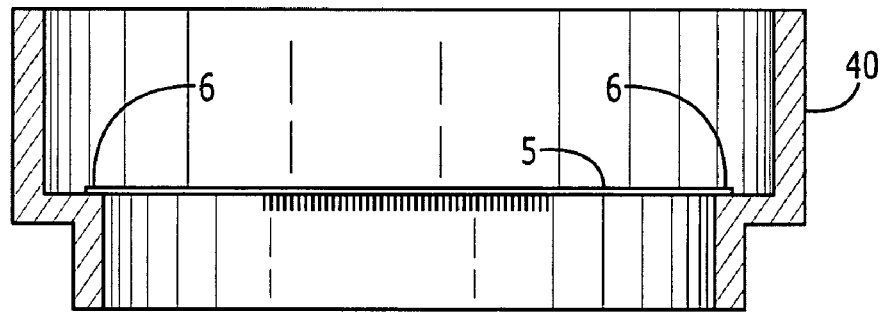
FIG. 4 is a side sectional view of a retainer having a microprojection member disposed therein.
Figure 5:
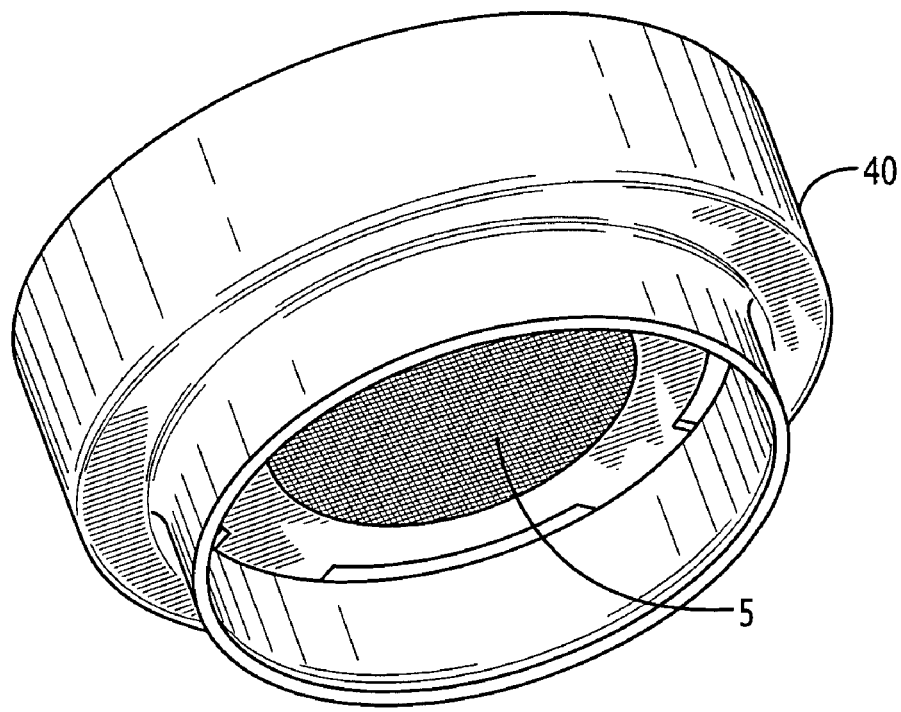
FIG. 5 is a perspective view of the retainer shown in FIG. 4.

Referring now to FIGS. 4 and 5, for storage and application, the microprojection member 5 is preferably suspended in a retainer ring 40 by adhesive tabs 6, as described in detail in Co-Pending U.S. application Ser. No. 09/976,762 (Pub. No. 2002/0091357), which is incorporated by reference herein in its entirety.

After placement of the microprojection member 5 in the retainer ring 40, the microprojection member 5 is applied to the patient's skin. Preferably, the microprojection member 5 is applied to the skin using an impact applicator, such as disclosed in Co-Pending U.S. application Ser. No. 09/976,798, which is incorporated by reference herein in its entirety.

As will be appreciated by one having ordinary skill in the art, the present invention can also be employed with the transdermal drug delivery system and apparatus disclosed in Co-Pending Application No. 60/514,433.

EXAMPLES

The following examples are given to enable those skilled in the art to more clearly understand and practice the present invention. They should not be considered as limiting the scope of the invention but merely as being illustrated as representative thereof.

Example 1

An aqueous solution containing 40 wt. % nicotine hydrogen tartrate was prepared. Sufficient fluorescein was added to the solution to generate a 0.001 M concentration. This agent was used to assess the quality of the coating after drying.

A strip of titanium foil was prepared by washing the surface with acetone and drying. Five microliters of the coating solution (or formulation) was applied and dried for four hours at room temperature. The quality of the coating was very poor when viewed under a fluorescent microscope, demonstrating poor wetting properties of the nicotine solution. When 0.1 wt. % hydroxyethyl cellulose (NATROSOL® 250 HHX PHARM, HERCULES Int. Lim., Netherlands, determined molecular weight: Mw 1890000, Mn 1050000) was added to the same coating solution, the coating noticeably improved.

Example 2

A 30 wt. % nicotine HCl solution is prepared in water. To that solution is added 0.1 wt. % hydroxyethyl cellulose and 0.2 wt. % of the surfactant Tween 20. The coating solution is then applied to the microprojections using the coating methods described in U.S. Publication No. 2002/0132054. The coating is evaluated and found to be well distributed across the projections. The coated and dried projections of a 2 $cm^2$ device is found to contain ca. 300 micrograms of nicotine HCl. When the device is applied in humans using the applicator described in U.S. Publication 2002/0123675, delivery of more than 70% of the nicotine contained on the projections is achieved.

Example 3

An aqueous solution consisting of 5 wt. % nicotine base, 5 wt. % hydroxypropyl methylcellulose (HPMC, Methocel E5 premium LV EP JP, Dow Chemical Company, Midland Mich.) and 0.2 wt. % Tween 20 is prepared. The coating solution is then applied to the microprojections using the coating methods described in U.S. Publication No. 2002/0132054. The coating is evaluated and found to be well distributed across the projections. The coated and dried projections of a 2 $cm^2$ device is found to contain ca. 400 micrograms of nicotine base. Application of the device to the skin results in the essentially immediate delivery of 300 micrograms nicotine base to the user.

From the foregoing description, one of ordinary skill in the art can easily ascertain that the present invention, among other things, provides an effective and efficient means for transdermally delivering nicotine-based agents to a tobacco user to substantially reduce or eliminate the tobacco usage habit.

As will be appreciated by one having ordinary skill in the art, the present invention provides many advantages. Among the advantages are:

Effective transdermal bolus delivery of nicotine-based agents;

Rapid administration or on-set of nicotine;

Effective treatment for break-through craving during tobacco quit attempts by administering small amounts of nicotine when needed; and Convenient method for supplementing nicotine replacement therapy employing a patch system.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An apparatus for transdermally delivering nicotine-based agents to a nicotine user, comprising a microprojection member having a plurality of microprojections that are adapted to pierce said nicotine user's stratum corneum for bolus delivery of at least one nicotine-based agent, said microprojection member including a biocompatible coating having at least one nicotine-based agent; wherein a total amount of the nicotine-based agent coated on the microprojections is sufficient to effectively deliver in the range of approximately 0.02-2.0 mg of the agent to the nicotine user, and wherein the composition of the coating is selected to deliver at least 50% of the total amount of the nicotine-based agent coated on the microprojection into the skin of the user one hour or less following application of the microprojection member to the user's skin.

2. The apparatus of claim 1, wherein said nicotine-based agent is selected from the group consisting of nicotine base, nicotine salts and simple derivatives of nicotine.

3. The apparatus of claim 1, wherein each of said microprojections has a length less than approximately 1000 microns.

4. The apparatus of claim 3, wherein each of said microprojections has a length less than approximately 500 microns.

5. The apparatus of claim 4, wherein each of said microprojections has a length less than approximately 250 microns.

6. The apparatus of claim 1, wherein said biocompatible coating further includes at least one wetting agent.

7. The apparatus of claim 1, wherein said biocompatible coating further includes a hydrophilic polymer.

8. The apparatus of claim 1, wherein said biocompatible coating further includes a surfactant.

9. The apparatus of claim 1, wherein said bio compatible coating further includes an amphiphilic polymer.

10. The apparatus of claim 1, where said biocompatible coating further includes a vasoconstrictor.

11. The apparatus of claim 1, wherein said biocompatible coating further includes a biocompatible carrier.

12. The apparatus of claim 1, wherein said biocompatible coating has a thickness less than approximately 50 microns.

13. The apparatus of claim 1, wherein said biocompatible coating has a thickness less than approximately 25 microns.

14. The apparatus of claim 1, further including an applicator having a contacting surface, wherein said microprojection member is releasably mounted on said applicator by a retainer and wherein said applicator, once activated, brings said contacting surface into contact with said microprojection member in such a manner that said microprojection member strikes the stratum corneum of the nicotine user with a power of at least 0.05 joules per cm.sup.2 of the microprojection member in 10 milliseconds or less.

15. A method for transdermally delivering a nicotine-based agent to a nicotine user, comprising the steps of:

providing a microprojection member having a plurality of microprojections that are adapted to pierce said nicotine user's stratum corneum for bolus delivery of at least one nicotine-based agent, said microprojections including a biocompatible coating having at least one nicotine-based agent; wherein a total amount of the nicotine-based agent coated on the microprojections is sufficient to effectively deliver in the range of approximately 0.02-2.0 mg of the agent to the nicotine user; and applying said microprojection member to said nicotine user's skin, whereby said microprojection members pierce said stratum corneum and deliver said nicotine-based agent, and wherein the composition of the coating is selected to deliver at least 50% of the total amount of the nicotine-based agent coated on the microprojection into the skin of the user one hour or less following application of the microprojection member to the user's skin.

16. The method of claim 15, wherein said biocompatible coating is applied to said microprojection member by immersing said microprojections in a coating formulation.

17. The method of claim 15, wherein said biocompatible coating is applied to said microprojection member by spraying a coating formulation onto said microprojections.

18. The method of claim 15, further comprising the steps of:

providing an applicator having a contacting surface, wherein said microprojection member is releasably mounted on said applicator by a retainer; and activating said applicator to bring said contacting surface into contact with said microprojection member in such a manner that said microprojection member strikes the stratum corneum of a nicotine user.

* * * * *